United States Patent [19]

Shanahan et al.

[11] Patent Number: 5,454,965
[45] Date of Patent: Oct. 3, 1995

[54] TELOMERIZED TRIGLYCERIDE OIL PRODUCT

[75] Inventors: Alka Shanahan, Seattle, Wash.; Phillip S. Landis, Alexandria, Va.

[73] Assignee: International Lubricants, Inc., Seattle, Wash.

[21] Appl. No.: 108,477

[22] Filed: Aug. 18, 1993

[51] Int. Cl.⁶ .................. C10M 129/74; C10M 129/68
[52] U.S. Cl. .................. 252/57; 554/25; 554/163; 560/116; 560/127
[58] Field of Search .................. 252/57; 554/25, 554/163; 560/116, 127

[56] References Cited

U.S. PATENT DOCUMENTS

| | | | |
|---|---|---|---|
| 2,212,385 | 8/1940 | Brod | 554/25 |
| 2,228,154 | 1/1941 | Priester | 554/25 |
| 2,373,015 | 4/1945 | Cowan et al. | 554/25 |
| 3,586,727 | 6/1971 | Wilke et al. | 560/116 |
| 5,229,023 | 7/1993 | Landis | 252/57 |

*Primary Examiner*—Jerry D. Johnson
*Attorney, Agent, or Firm*—Jeffrey B. Oster

[57] ABSTRACT

There is disclosed an improved telomerized oil comprising no more than 4% polyunsaturated fatty acids and a plurality of aliphatic rings, wherein the improved telomerized oil is made from about 20% to about 70% of a conjugated triglyceride oil, wherein the conjugated triglyceride oil has at least 50% of fatty acids having at least two conjugated double bonds and from about 30% to about 80% of a vegetable triglyceride oil, wherein the vegetable triglyceride oil has from about 10% to about 75% of its fatty acids being polyunsaturated and having from about 16 to about 26 carbon atom chain length (unbranched). The present invention further provides an improved telomerized oil produced by a process comprising heating from about 20% to about 70% of a conjugated triglyceride oil, wherein the conjugated triglyceride oil has at least 50% of fatty acids polyunsaturated with at least two conjugated double bonds and from about 30% to about 80% of a vegetable triglyceride oil, wherein the vegetable triglyceride oil has from about 10% to about 75% of its fatty acids being polyunsaturated and having from about 16 to about 26 carbon atom chain length (unbranched), in a non-oxidizing atmosphere at from about 150° C. to about 400° C. for from about 3 hours to about 10 hours to lower the amount of polyunsaturation in the conjugated triglyceride oil and vegetable triglyceride oil to less 4% through the formation of aliphatic rings. The present invention further provides a process for synthesizing an improved telomerized oil, comprising heating from about 20% to about 70% of a conjugated triglyceride oil, wherein the conjugated triglyceride oil has at least 50% of fatty acids polyunsaturated with at least two conjugated double bonds and from about 30% to about 80% of a vegetable triglyceride oil, wherein the vegetable triglyceride oil has from about 10% to about 75% of its fatty acids being polyunsaturated and having from about 16 to about 26 carbon atom chain length (unbranched), in a non-oxidizing atmosphere at from about 150° C. to about 400° C. for from about 3 hours to about 10 hours to lower the amount of polyunsaturation in the conjugated triglyceride oil and vegetable triglyceride oil to less 4% through the formation of aliphatic rings.

16 Claims, No Drawings

TELOMERIZED TRIGLYCERIDE OIL PRODUCT

TECHNICAL FIELD OF THE INVENTION

The present invention provides lubricant compositions and lubricant ingredients comprising an improved telomerized oil product. More specifically, the present invention provides a telomerized oil product that is telomerized from a polyunsaturated triglyceride plant-derived oil that predominantly comprises fatty acids having conjugated double bonds. The present invention further provides derivative lubricant products and ingredients made from a polyunsaturated triglyceride plant-derived oil that predominantly comprises fatty acids having conjugated double bonds.

BACKGROUND OF THE INVENTION

The field of lubricant additives has seen a wide variety of materials used to reduce friction and wear between moving parts. Lubricants are composed principally of a base stock and a lubricant additive. The lubricant additive provides the antifriction and antiwear characteristics to the lubricant. The base stock imparts improved viscosity and thermal oxidative stability, which can be improved by the addition of various additives. One significant advance in the field was the invention of a material called a "telomer". The telomer invention is described in WO92/07051 and in U.S. Pat. No. 5,229,023, the disclosure of which is incorporated by reference herein.

Briefly, a telomer is a polymerized triglyceride oil, principally derived from a seed oil, that has thermal oxidative stability and viscosity improvement characteristics that makes the telomer an essential component of a large variety of lubricant compositions. The process to synthesize telomers begins with a triglyceride and heats the oil in a non-oxidizing atmosphere with a trace water catalyst to lower the iodine number such that no more than 4% of the fatty acid chains of the telomerized vegetable oil are polyunsaturated. The triglyceride vegetable oils are characterized as having from about 10% to about 75% polyunsaturated fatty acid chains of from about 16 to about 26 carbon atoms in length.

The present invention was made in an effort to improve the telomer product by lowering temperature of formation and time of heating and by improving viscosity and color characteristics of the telomer product.

SUMMARY OF THE INVENTION

The present invention provides an improved telomer product and an improved process for synthesizing the telomer product. More specifically, the present invention provides a triglyceride oil wherein at least 50% of the fatty acids comprise at least two conjugated double bonds that is formed into a telomer by heating the oil for from about 3 hours to about 10 hours at a temperature of from about 150° C. to about 400° C. Preferably, at least 50% of the fatty acids comprise at least three conjugated double bonds. The improved telomer product is useful as an antiwear agent and as a thickening agent in lubricant compositions.

The present invention provides an improved telomerized oil comprising no more than 4% polyunsaturation and a plurality of aliphatic rings, wherein the telomerized oil is made from about 20% to about 70% of a conjugated triglyceride oil, wherein the conjugated triglyceride oil has at least 50% of fatty acids having at least two conjugated double bonds and from about 30% to about 80% of a vegetable triglycericle oil, wherein the vegetable triglyceride oil has from about 10% to about 75% of its fatty acids being polyunsaturated and having from about 16 to about 26 carbon atom chain length (unbranched). Preferably, the conjugated triglyceride oil comprises at least 50% of fatty acids having at least three conjugated double bonds. The present invention further provides an improved telomerized oil produced by a process comprising heating from about 20% to about 70% of a conjugated triglyceride oil, wherein the conjugated triglyceride oil has at least 50% of fatty acids polyunsaturated with at least two conjugated double bonds and from about 30% to about 80% of a vegetable triglyceride oil, wherein the vegetable triglyceride oil has from about 10% to about 75% of its fatty acids being polyunsaturated and having from about 16 to about 26 carbon atom chain length (unbranched), in a non-oxidizing atmosphere at from about 150° C. to about 400° C. for from about 3 hours to about 10 hours to lower the total number of polyunsaturated fatty acids in the conjugated triglyceride oil and vegetable triglyceride oil to less than 10% through the formation of aliphatic rings. Preferably the conjugated triglyceride oil comprises at least three conjugated double bonds in at least 50% of its fatty acids. Preferably, the conjugated triglyceride oil is heated in the presence of trace amounts of water vapor to serve as a catalyst. Preferably, the total number of polyunsaturated fatty acids in the improved telomerized oil is less than 4%.

The present invention further provides a process for synthesizing an improved telomerized oil, comprising heating from about 20% to about 70% of a conjugated triglyceride oil, wherein the conjugated triglyceride oil has at least 50% of fatty acids polyunsaturated with at least two conjugated double bonds and from about 30% to about 80% of a vegetable triglyceride oil, wherein the triglyceride vegetable oil has from about 10% to about 75% of its fatty acids being polyunsaturated and having from about 16 to about 26 carbon atom chain length (unbranched), in a non-oxidizing atmosphere at from about 150° C. to about 400° C. for from about 3 hours to about 10 hours to lower the total number of polyunsaturated fatty acids in the conjugated triglyceride oil and vegetable triglyceride oil to less 4% through the formation of aliphatic rings. Preferably the conjugated triglyceride oil comprises at least three conjugated double bonds in at least 50% of its fatty acids. Preferably, the conjugated triglyceride oil is heated in the presence of trace amounts of water vapor to serve as a catalyst.

DETAILED DESCRIPTION OF THE INVENTION

The present invention represents a surprising improvement over the telomer oil art and provides an improved telomerized oil using a process that requires a lower processing temperature and a faster reaction time than the original telomer invention described in U.S. Pat. No. 5,229,023, the disclosure of which is incorporated by reference herein. Moreover, the present invention provides an improved telomerized oil having improved viscosity, lighter color and a lower acid number than the telomerized oil described in U.S. Pat. No. 5, 229,023. The telomerized oil described in U.S. Pat. No. 5, 229,023 is characterized as the product of heating a vegetable triglyceride oil for at least 5 hours at a temperature of from about 200° C. to about 400° C. to lower the number of polyunsaturated fatty acids to less than 4% of the total number of fatty acids through formation of aliphatic rings, wherein the vegetable triglyceride oil has from about 10% to about 75% of its fatty acids being polyunsaturated and having from about 16 to about 26 carbon atoms chain lengths. Several appropriate vegetable triglyceride oils were illustrated, such as those vegetable triglyceride oils selected from the group consisting of rapeseed oil, crambe oil, meadowfoam oil, soya bean oil, peanut oil, corn oil, safflower oil, sunflower seed oil, cottonseed oil, olive oil, coconut oil, palm oil, linseed oil, and combinations thereof.

The present invention found a surprising improvement in the properties and processing characteristics of the resulting telomerized oil by mixing from about 20% to about 70% of a conjugated triglyceride oil into the vegetable triglyceride oil for heating to form the telomerized oil. The conjugated triglyceride oil has at least 50% of fatty acids having at least two conjugated double bonds. Preferably, the conjugated triglyceride oil has at least three conjugated double bonds. By a conjugated double bond, this terms refers to a fatty acid having an alternating single bond and double bond along the hydrocarbon chain. The resulting improved telomerized oil has increased viscosity, increased solubility in a variety of lubricant base oils, is lighter in color and has a lower acid number (a measure of the amount of free fatty acids present). The lighter color will provide greater consumer acceptance, as darker colors denote a more oxidized product. Also, the acid number is an indication of oxidation breakdown, so it is desirable to have a product start with a lower acid number, especially when the material is to be used in a lubricant operating in a high temperature environment, such as an engine oil. Moreover, the resulting improved telomerized oil can be processed at a lower temperature and will telomerize faster resulting in a shorter reaction time. This provides significant energy savings and reduced processing and operating costs operating at a lower temperature for a shorter time.

The essential characteristic of the conjugated triglyceride oil is the presence of conjugated double bonds in at least 50% of the fatty acids in the triglyceride oil. Examples of appropriate conjugated triglyceride oils include, for example, tung oil, oiticica oil, seed fats of Rosaceae, Euphorbiaceae, and Cucurbitaceae families, fish oils enriched in ω-3 fatty acids, and combinations thereof. Tung oil was used as an example of a conjugated triglyceride oil. Tung oil is made from kernels of the fruit of the tung tree, which has been grown in China for centuries and more recently (since 1925) grown in southeastern United States. The tung kernels have about a 17.5% oil content. Tung oil generally has a saponification number of 189 195, an iodine number of 160–175, an R.I. at 25° C. of 1.516–1.520 and unsaponified matter below 1%. The fatty acid profile of tung oil is shown in Table 1 below.

TABLE 1

| Fatty Acid | Percent (%) |
| --- | --- |
| oleic acid | 4–9 |
| linoleic acid | 8–10 |
| saturated | 2–6 |
| α-eleostearic acid | 77–86 |
| linolenic acid | trace |

α-Eleostearic acid is a conjugated fatty acid, such as 9,11,13-octadecatrienoic acid, and linolenic acid is predominantly (not conjugated) 9,12,15-octadecatrienoic acid. The cold water fish oils (and cod liver oil) contain high levels of the polyunsaturated fatty acids eicosapentenoic acid and docosahexaenoic acid.

There is a need to improve the viscosity of lubricant products such that the viscosity of the lubricant product does not break down when operating at high temperatures (such as an engine oil). Such ingredients are called "VI" improvers for viscosity index. There is a problem with VI improvers that are not soluble in a variety of base oils, such as various mineral oil bases and seed oil base oils. The improved telomerized oil has greater solubility in a variety of base oils that a telomerized vegetable oil, including solubility in a seed oil (HEAR oil, a rapeseed oil), a napthenic oil, a paraffinic oil and a eicosyl erucate linear liquid wax ester (EG-20 oil).

A group of telomerized vegetable oils and improved telomerized oils were made. The raw materials, reaction time, and reaction temperatures are listed in Table 2 below:

TABLE 2

| | Raw Material (wt. %) | | | | |
| --- | --- | --- | --- | --- | --- |
| Product | Tung oil | Linseed oil | HEAR | Temp °C. | Time (hr) |
| A | 0 | 50 | 50 | 320 | 6 |
| B | 0 | 50 | 50 | 293 | 6 |
| C | 50 | 0 | 50 | 293 | 6 |
| D | 40 | 0 | 60 | 293 | 6 |
| E | 50 | 0 | 50 | 293 | 6 |
| F | 30 | 35 | 35 | 293 | 6 |
| G | 30 | 35 | 35 | 303 | 6 |
| H | 40 | 0 | 60 | 293 | 6 |
| I | 0 | 50 | 50 | 320 | 24 |

Telomerized oils A and B are vegetable telomerized oils described in U.S. Pat. No. 5,229,023. Telomerized oils C-H are improved telomerized oils. The results of KV (kinematic viscosity), acid number (mg KOH/g) and solubility at 5% in a variety of base oils show the improved properties of the improved telomerized oil. Table 3 below illustrate these data.

TABLE 3

| | KV @40 | Acid | Solubility @5% | | | |
| --- | --- | --- | --- | --- | --- | --- |
| Oil | °C. (sus) | No. | EG-20 | Naphthenic | Paraffinic | HEAR |
| A | 2636 | 23.99 | clear | clear | clear | clear |
| B | 646 | 7.65 | clear | clear | clear | clear |
| C | 41,328 | 5.79 | clear | clear | clear | clear |
| D | 6387 | 4.99 | clear | clear | clear | clear |
| E | 56,760 | 5.21 | clear | clear | clear | clear |
| F | 13,330 | 4.68 | clear | clear | clear | clear |
| G | 17,634 | 10.1 | clear | clear | clear | clear |
| H | 6848 | 4.85 | clear | clear | clear | clear |
| I | 10,000 | 49.3 | clear | clear | hazy | clear |

For the solubility measurements, naphthenic oil was a Shell MVI oil, paraffinic oil was a Mohawk 150, and EG-20 was a linear liquid was ester, and the HEAR oil used was a triglyceride rapeseed vegetable oil.

EXAMPLE 1

This example illustrates an evaluation of various properties of an improved telomer oil. The improved telomer oil was made from tung oil (50%) and HEAR (high erucic acid rapeseed oil) (50%), and heated to about 293° C. for a six hour reaction. The kinematic viscosity was 8922 (cSt) and 41328 (saybolt universal seconds, sus) at 40° C., and 3806 (cSt) and 17630 (sus) at 100° C., indicating a substantial improvement in viscosity over a telomer oil made with only HEAR and without a conjugated polyunsaturated tirglyceride oil. The acid value was 5.79 mg KOH/gm, and the color was golden yellow.

The solubility characteristics of the improved telomer oil are soluble (at 5%) in HEAR oil, EG-20 (a rapeseed oil-derived linear liquid wax ester), a naphthenic-based MVI (Shell), and a paraffinic-based MVI (Mohawk 150). As a comparison, a telomerized oil made without a conjugated polyunsaturated triglyceride oil and with rapeseed oil and a source of triglyceride linoleic acid was soluble at 5% in HEAR oil, EG-20, and the naphtheric-based MVI, but not the paraffinic-based MVI.

The improved telomer oil (called T-41000), a telomerized vegetable oil (product A in Table 2), and a commercially available VI improver (Acryloid 1019, a polymethacrylate based and shear stable VI improver, kinematic viscosity of 800±150 cST at 100° C.) were compared for thickening effect at 2% in a typical MVI oil (Shell). Both product significantly improved the kinematic viscosity of the final blend. The comparison are present in Table 4 below:

TABLE 4

| Kinematic Viscosity | MVI | MVI + 2% T-41000 | MVI + 4% Prod. A | MVI + 2% Acryloid |
| --- | --- | --- | --- | --- |
| cSt @ 40° C. | 22.36 | 25.81 | 24.52 | 24.77 |
| cSt @ 100° C. | 4.06 | 4.58 | 4.43 | 4.53 |
| Viscosity Index | 61 | 85 | 83 | 92 |

EXAMPLE 2

This example illustrates a comparison of antiwear characteristics of a telomerized vegetable oil and an inventive improved telomer oil. The telomerized vegetable oil and improved telomer oil are described in Example 1. Antiwear properties were determined using a Falex Pin and Vee Block method (ASTM D-2670). One percent of each telomer oil was mixed into a base fluid, consisting of Mohawk 150 oil (30%), bright stock (69.75%) and Mobil E.P additive (0.25%) by weight. The results (presented in Table 5 below) show improved antiwear properties of the improved telomer oil over the vegetable oil telomerized oil.

TABLE 5

| Sample | Teeth Wear | % Reduction |
| --- | --- | --- |
| Base fluid control | 71 | — |
| 1% Vegetable Oil Telomer | 30 | 57.7% |
| 1% Improved Telomer Oil | 8 | 89 |

Therefore, the improved telomer exhibits improved antiwear characteristics over the original vegetable oil telomer, yet still retains its viscosity improvement and thermal oxidative stability characteristics.

We claim:

1. An improved the telomerized oil comprising no more than 4% polyunsaturated fatty acids and a plurality of aliphatic rings, wherein the improved telomerized oil is made from about 20% to about 70% of a conjugated triglyceride oil, wherein the conjugated triglyceride oil has at least 50% of fatty acids having at least two conjugated double bonds and from about 30% to about 80% of a triglyceride vegetable oil, wherein the triglyceride vegetable oil has from about 10% to about 75% of its fatty acids being polyunsaturated and having from about 16 to about 26 carbon atom chain length (unbranched).

2. The improved telomerized oil of claim 1, wherein the conjugated triglyceride oil comprises at least 50% of fatty acids having at least three conjugated double bonds.

3. The improved telomerized oil of claim 1, wherein the conjugated triglyceride oil is tung oil, fish oils enriched in ω-3 fatty acids, cod liver oil, and combinations thereof.

4. The improved telomerized oil of claim 3, wherein the fish oils enriched in 03-3 fatty acids are selected from the group consisting of salmon oil, herring oil, menhaden oil, sardine oil, pollack oil, and combinations thereof.

5. The improved telomerized oil of claim 1, wherein the vegetable triglyceride oil is rapeseed oil, crambe oil, meadowfoam oil, soya bean oil, peanut oil, corn oil, safflower oil, sunflower seed oil, cottonseed oil, olive oil, coconut oil, palm oil, linseed oil, and combinations thereof.

6. An improved telomerized oil produced by a process comprising heating from about 20% to about 70% of a conjugated triglyceride oil, wherein the conjugated triglyceride oil has at least 50% of fatty acids polyunsaturated with at least two conjugated double bonds and from about 30% to about 80% of a vegetable triglyceride oil, wherein the vegetable triglyceride oil has from about 1.0% to about 75% of its fatty acids being polyunsaturated and having from about 16 to about 26 carbon atom chain length (unbranched), in a non-oxidizing atmosphere for from about 150° C. to about 400° C. for from about 3 hours to about 10 hours to lower the total number of polyunsaturated fatty acids in the conjugated triglyceride oil and the vegetable triglyceride oil to less than 10% through the formation of aliphatic rings.

7. The improved telomerized oil of claim 6, wherein the conjugated triglyceride oil comprises at least 50% of fatty acids having at least three conjugated double bonds.

8. The improved telomerized oil of claim 6, wherein the conjugated triglyceride oil is tung oil, fish oils enriched in ω-3 fatty acids, cod liver oil, and combinations thereof.

9. The improved telomerized oil of claim 8, wherein the fish oils enriched in ω-3 fatty acids are selected from the group consisting of salmon oil, herring oil, menhaden oil, sardine oil, pollack oil, and combinations thereof.

10. The improved telomerized oil of claim 6, wherein the vegetable triglyceride oil is rapeseed oil, crambe oil, meadowfoam oil, soya bean oil, peanut oil, corn oil, safflower oil, sunflower seed oil, cottonseed oil, olive oil, coconut oil, palm oil, linseed oil, and combinations thereof.

11. A process for synthesizing an improved telomerized oil, comprising heating from about 20% to about 70% of a conjugated triglyceride oil, wherein the conjugated triglyceride oil has at least 50% of fatty acids polyunsaturated with at least two conjugated double bonds and from about 30% to about 80% of a vegetable triglyceride oil, wherein the vegetable triglyceride oil has from about 10% to about 75% of its fatty acids being polyunsaturated and having from about 16 to about 26 carbon atom chain length, in a non-oxidizing atmosphere at from about 150° C. to about 400° C. for from about 3 hours to about 10 hours to lower the amount of polyunsaturation in the conjugated triglyceride oil and vegetable triglyceride oil to less than 4% through the formation of aliphatic rings.

12. The process of claim 11, wherein the conjugated triglyceride oil and vegetable triglyceride oil are heated in the presence of trace amounts of water vapor to serve as a catalyst.

13. The process of claim 11, wherein the conjugated triglyceride oil comprises at least 50% of fatty acids having at least three conjugated double bonds.

14. The process of claim 11, wherein the conjugated triglyceride oil is tung oil, fish oils enriched in ω-3 fatty acids, cod liver oil, and combinations thereof.

15. The process of claim 14, wherein the fish oils enriched in ω-3 fatty acids are selected from the group consisting of salmon oil, herring oil, menhaden oil, sardine oil, pollack oil, and combinations thereof.

16. The process of claim 11, wherein the vegetable triglyceride oil is rapeseed oil, crambe oil, meadowfoam oil, soya bean oil, peanut oil, corn oil, safflower oil, sunflower seed oil, cottonseed oil, olive oil, coconut oil, palm oil, linseed oil, and combinations thereof.

* * * * *